United States Patent [19]

Bresson et al.

[11] Patent Number: 4,515,687

[45] Date of Patent: May 7, 1985

[54] ORE FLOTATION AND FLOTATION AGENTS FOR USE THEREIN

[76] Inventors: Clarence R. Bresson; Rector P. Louthan, both of c/o French, Hughes and Doescher, P.O. Box 2443, Bartlesville, Okla. 74005

[21] Appl. No.: 608,825

[22] Filed: May 10, 1984

[51] Int. Cl.$^3$ .......................... B03D 1/06; C09K 3/00; C22B 3/00; C07C 154/02

[52] U.S. Cl. .................................... 209/167; 209/166; 252/61; 260/455 B; 568/63; 568/69

[58] Field of Search .................. 252/61; 209/166, 167; 260/455 B; 568/63, 69

[56] References Cited

U.S. PATENT DOCUMENTS 2,197,964 4/1940 Bishop ............................ 260/455 B 3,660,412 5/1972 Haugwitz ........................ 260/455 B 4,136,020 1/1979 Fischer .................................. 252/61

4,410,439 10/1983 Crozier ................................ 252/61

*Primary Examiner*—Paul Lieberman

*Assistant Examiner*—Robert A. Wax

[57] ABSTRACT

Ammonium dialkylaminoalkyl (thiocarbonyldithio) alkanoates, alkali metal dialkylaminoalkyl (thiocarbonyldithio) alkanoates, their use as flotation agents, and a process for the production of these novel compositions are disclosed. N,N-dialkylaminoalkyl mercaptoalkanoate, its use as an intermediate in the production of the novel ammonium dialkylaminoalkyl (thiocarbonyldithio) alkanoates and alkali metal dialkylaminoalkyl (thiocarbonyldithio) alkanoates, and a process for the production of this novel composition are also disclosed.

34 Claims, No Drawings

ORE FLOTATION AND FLOTATION AGENTS FOR USE THEREIN

This invention relates generally to novel chemical compositions. In one aspect, the invention relates to a process for making such compositions. In another aspect, the invention relates to ore flotation processes employing such novel compositions.

Froth flotation is a process for recovering and concentrating minerals from ores. In a froth flotation process the ore is crushed and wet ground to obtain a pulp. Additives such as mineral flotation or collecting agents, frothing agents, suppressants, stabilizers, etc. are added to the pulp to assist in separating valuable minerals from the undesired or gangue portions of the ore in subsequent flotation steps. The pulp is then aerated to produce a froth at the surface. The minerals which adhere to the bubbles or froth are skimmed or otherwise removed and separated. Selective suppressants or depressants inhibit the adherence of certain minerals to the bubbles or froth thus assisting in the separation of the froth product from the reject product which includes those minerals suppressed by the suppressant agent. The froth product or the reject product or both can then be further processed to obtain the desired minerals, such as by additional flotation stages. Generally the ore is initially floated to produce a rougher concentrate, the rougher concentrate thereafter being refloated in the presence of suppressants to further separate the minerals therein. Typical mineral flotation collectors include xanthates, amines, alkyl sulfates, arenes, sulfonates, dithiocarbamates, dithiophosphates, and thiols.

It is known from the art that some organic derivatives of trithiocarbonic acid are useful as flotation agents. U.S. Pat. No. 1,659,396, for instance, describes diethyltrithiocarbonate and the production thereof. U.S. Pat. No. 3,166,580 describes dicyclopentyl trithiocarbonates and their production as well as the utility of these compounds a flotation agents.

It is a continuing goal in the ore-processing industry to increase the productivity of ore flotation processes and, above all, to provide specific procedures which are selective to one ore or metal over other ores or metals present in the treated material.

It is an object of the invention to provide a novel composition of matter.

Another object of the invention is to provide new trithiocarbonates.

A further object of the invention is to provide a process for producing such new trithiocarbonates.

Yet another object of the invention is to provide an improved ore flotation process wherein such new trithiocarbonates are used as flotation agents.

Still another object of the invention is to provide a novel suppressant suitable for use in an ore flotation process.

These and other objects, advantages, details, features and embodiments of this invention will become apparent to those skilled in the art from the following detailed description of the invention and the appended claims.

In accordance with this invention it has been found that ammonium dialkylaminoalkyl(thiocarbonyldithio)alkanoates and alkali metal dialkylaminoalkyl(thiocarbonyldithio)alkanoates are novel compositions and are very effective and selective ore flotation agents.

Thus, in accordance with a first aspect of this invention, novel compositions of matter are provided which can be characterized by the formula $$R^1R^2NR^3O\overset{O}{\overset{\|}{C}}R^4S-\overset{S}{\overset{\|}{C}}-S-M,$$

wherein M is selected from the group consisting of ammonium and alkali metals from Group IA of the Periodic Table of the Elements, wherein $R^1$ is an alkyl radical, $R^2$ is an alkyl radical, $R^3$ is an alkylene radical, $R^4$ is an alkylene radical, and $R^1$ and $R^2$ can be the same or different.

In accordance with another aspect of this invention, novel compositions of matter are provided which can be characterized by the formula $$R^1R^2NR^3O\overset{O}{\overset{\|}{C}}R^4SH,$$

wherein $R^1$ is selected from the group consisting of alkyl radicals, $R^2$ is selected from the group consisting of alkyl radicals, $R^3$ is selected from the group consisting of alkylene radicals, and $R^4$ is selected from the group consisting of alkylene radicals, and $R^1$ and $R^2$ can be the same or different.

In accordance with yet another aspect of this invention there is provided a process for producing the above-defined novel compositions. This process comprises reacting $H_2S$ with a composition having the formula $$R^1R^2NR^3O\overset{O}{\overset{\|}{C}}X, \qquad \text{(I)}$$

wherein $R^1$ is selected from the group consisting of alkyl radicals, $R^2$ is selected from the group consisting of alkyl radicals, $R^3$ is selected from the group consisting of alkylene radicals, and X is selected from the group consisting of alkenyl radicals, to form the novel composition having the formula $$R^1R^2NR^3O\overset{O}{\overset{\|}{C}}R^4SH, \qquad \text{(II)}$$

wherein $R^4$ is selected from the group consisting of alkylene radicals. This novel process is characterized further to include reacting the composition of formula (II) with $CS_2$ and a hydroxide having the formula $$MOH \qquad \text{(III)},$$

wherein M is selected from the group consisting of ammonium and alkali metals from Group IA of the Periodic Table of the Elements to form the novel composition having the formula $$R^1R^2NR^3O\overset{O}{\overset{\|}{C}}R^4S-\overset{S}{\overset{\|}{C}}-S-M, \qquad \text{(IV)}$$

and recovering the composition of formula (IV) as the product of the process.

Suitable reagents represented by the formula (I) above include, but are not limited to N,N-diethylaminoethyl acrylate.

The detailed operating conditions for the individual steps of the process of the present invention are not critical and specific values for the steps can be seen from the following examples. Generally, the first step of the process, namely the reaction of the dialkylaminoalkylacrylate of formula (I) with $H_2S$ can be satisfactorily carried out in an aqueous environment, optionally including isopropyl alcohol, at a temperature in the range from about 25° C. to about 125° C. and under a pressure of from about 0° to about 500 psig. for a time in the range from about 1 to about 10 hours. Recovery of the resulting product of formula (II) can be carried out by standard techniques, such as distillation, if desired. The reaction of the product of formula (II) with the alkali metal hydroxide or ammonium hydroxide and carbon disulfide can also be suitably performed in an aqueous environment at a temperature in the range from about 25° C. to about 100° C. and at a pressure in the range from about 0 to about 500 psig. for a time in the range from about 1 to about 10 hours. The recovery of the product of formula (IV) can be carried out by standard techniques.

A further aspect of this invention resides in an ore flotation process. More specifically, such further aspect of this invention resides in a process for separating valuable ore materials from gangue materials. The ore flotation process of this invention distinguishes over the known ore flotation processes primarily in the employment of a new flotation agent to be defined. Otherwise, the recovery process involves crushing of the ore and ore grinding preparatory to mixing the thus ground ore and water to obtain a pulp. In this pulp the flotation agent is incorporated and the pulp is aerated to produce a froth at the surface which is rich in valuable ore materials but depleted of the gangue materials or vice versa. The ore materials, optionally, after additional flotation or frothing steps in which the novel flotation agent can be employed, are recovered. In addition to the novel flotation agent of the present invention, frothing agents, other selective suppressants and stabilizers which are known in the art can be used in the various steps. Generally the novel suppressant of the present invention will be advantageously employed in the flotation of a rougher concentrate following the use of a collector in a prior flotation step wherein Mo, Cu, Fe, etc. are separated as the rougher concentrate from the gangue materials in the ore.

The compositions useful as flotation agents in the ore flotation process of this invention are characterized by the formula $$R^1R^2NR^3O\overset{\overset{O}{\|}}{C}R^4S-\overset{\overset{S}{\|}}{C}-S-M,$$

wherein $R^1$ is selected from the group consisting of alkyl radicals, $R^2$ is selected from the group consisting of alkyl radicals, $R^3$ is selected from the group consisting of alkylene radicals, $R^4$ is selected from the group consisting of alkylene radicals, and M is selected from the group consisting of ammonium and alkali metals from Group IA of the Periodic Table of the Elements.

It is presently preferred that the alkyl radicals of $R^1$ and $R^2$ each have from 1 to 6 carbon atoms. The alkyl radicals of $R^1$ and $R^2$ can be linear or branched. It is presently preferred that the alkylene radicals of $R^3$ each have from 1 to 6 carbon atoms and that the alkylene radicals of $R^4$ each have from 2 to 6 carbon atoms. The alkylene radicals $R^3$ and $R^4$ can be linear or branched. Examples of such compounds useful as flotation agents in the process of this invention are those generally characterized as ammonium dialkylaminoalkyl(thiocarbonyldithio)alkanoate and alkali metal dialkylaminoalkyl(thiocarbonyldithio)alkanoate, such as, for example,

- sodium N,N-diethylaminoethyl-3-(thiocarbonyldithio)-propionate,
- ammonium N,N-diethylaminoethyl-3-(thiocarbonyldithio)-propionate,
- potassium N,N-diethylaminoethyl-3-(thiocarbonyldithio)-propionate,
- lithium N,N-diethylaminoethyl-3-(thiocarbonyldithio)-propionate, and the like, and mixtures of any two or more thereof. The presently preferred composition used as the flotation agent in the process of this invention is sodium N,N-diethylaminoethyl-3-(thiocarbonyldithio)propionate.

The amount of ammonium dialkylaminoalkyl(thiocarbonyldithio)alkanoate and/or alkali metal dialkylaminoalkyl(thiocarbonyldithio)alkanoate employed in the mineral recovery process of this invention is not critical. The quantity will depend upon the process parameters. Generally, the novel ore flotation agent compositions of the present invention will be employed in the ore flotation mineral recovery process at concentration levels sufficient to provide the desired suppressant (or depressant) action on certain minerals. The amount of ammonium dialkylaminoalkyl(thiocarbonyldithio)alkanoate and/or alkali metal dialkylaminoalkyl(thiocarbonyldithio)alkanoate employed as a suppressant in the mineral recovery process of this invention will generally range from about 0.1 lb to about 10 lb of the ammonium dialkylaminoalkyl(thiocarbonylditho)alkanoate and/or alkali metal dialkylaminoalkyl(thiocarbonyldithio)alkanoate per ton of solids or crushed ore, and more preferably range from about 0.15 to about 6 lb/ton of solids or crushed ore. The novel suppressants or depressants of the present invention can be added to an ore flotation mineral recovery process or system at the ore-grinding stage, the ore flotation step and/or to the concentrate which is to be further floated.

Various flotation agents or processing aids can be used in conjunction with the novel suppressants of the present invention such as, for example, flocculents, frothers, dispersants, promoters and the like.

It is generally believed that the novel alkanoic compositions disclosed herein are useful for separating any valuable metal sulfide from its corresponding gangue material. It is also understood that the novel alkanoates can facilitate the separation of a mixture of metals that are contained in a particular mining deposit or ore, said mixture being further separated by subsequent froth flotations or any other conventional separating methods. The alkanoates herein disclosed are particularly useful as copper and/or iron suppressants in the separation of molybdenum minerals from the total ore. Examples of such molybdenum-bearing ores include, but are not limited to such materials as

| Molybdenum-Bearing ores: | |
|---|---|
| Molybdenite | $MoS_2$ |
| Wulfenite | $PbMoO_4$ |
| Powellite | $Ca(Mo,W)O_4$ |
| Ferrimolybdite | $Fe_2Mo_3O_{12}.8H_2O$ |

Other metal bearing ores within the scope of this invention are, for example, but are not limited to, such materials as

| | |
|---|---|
| Copper-bearing ores: | |
| Covellite | CuS |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_3SbS_2$ |
| Tennanite | $Cu_{12}As_4S_{13}$ |
| Cuprite | $Cu_2O$ |
| Tenorite | CuO |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Lead-Bearing ore: | |
| Galena | PbS |
| Antimony-Bearing ore: | |
| Stibnite | $Sb_2S_3$ |
| Zinc-Bearing ores: | |
| Sphalerite | ZnS |
| Zincite | ZnO |
| Smithsonite | $ZnCO_3$ |
| Chromium-Bearing ores: | |
| Daubreelite | $FeSCrS_3$ |
| Chromite | $FeO.Cr_2O_3$ |
| Iron-Bearing ores: | |
| Pyrite or Marcasite | $FeS_2$ |
| Pyrrhotite | $Fe_5S_6$ to $Fe_{16}S_{17}$ |
| Nickel-Bearing ores: | |
| Pentlandite | (FeNi)S |
| Millerite | NiS |
| Niccolite | NiAs |

The presently preferred ores in connection with which the process of this invention is applied are molybdenum, lead, copper and iron ores or minerals.

Separation Conditions

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in test conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of N,N-diethyl-2-aminoethyl-3-mercaptopropionate, a novel compound useful as an intermediate in the preparation of a product employed in ore flotation. To a one-gallon stainless steel reactor equipped with a stirrer, thermocouple and pressure gauge was added 612 grams (17.96 moles) of $H_2S$, 4.5 grams elemental sulfur, 115 milliliters of isopropyl alciohol and 6 milliliters of distilled water. With the reactor closed and stirrer on there was pumped in over about a 1 hour period 1026 grams (5.99 moles) of N,N-diethylaminoethyl acrylate (Agriflex ® from CPS). The initial temperature of 68° F. slowly rose to a maximum of 109° F. while the pressure dropped from 250 pounds per square inch gauge to 175 pounds per square inch gauge. There was obtained 1302 grams of a product mixture which was transferred to a flask equipped with a Vigreaux column and distilled. There was obtained 978 grams (4.76 moles, 79 mole percent yield) of a crude product distilling at 114°-126° C. at 5 millimeters pressure which was assumed to be the material N,N-diethyl-2-aminoethyl-3-mercaptopropionate.

EXAMPLE II

This example describes the preparation of the sodium trithiocarbonate derivative of the product prepared in Example I. To a one liter 3-neck flask fitted with a stirrer, reflux condenser and dropping funnel was added 205 grams (1.0 mole) of N,N-diethyl-2-aminoethyl-3-mercaptopropionate prepared in Example I and 378 milliliters of distilled water. The solution was slightly yellow in color and cloudy. To this stirred solution was added dropwise over a 10 to 12 minute period 76 grams (1.0 mole) of carbon disulfide. The solution turned a bright yellow with some crystal formation. A solution of 44 grams (1.1 moles) sodium hydroxide pellets in 98.5 grams of distilled water was then added slowly with stirring and external cooling so that the temperature was maintained below about 50° C. The reaction mixture became homogenous and turned orange in color. The reaction product mixture was considered to contain as the active ingredient 40 weight percent sodium trithiocarbonate derivative of N,N-diethyl-2-aminoethyl-3-mercaptopropionate also referred to as sodium N,N-diethylaminoethyl-3-(thiocarbonyldithio)propionate.

EXAMPLE III

This example describes the procedure used to evaluate the reaction product mixture from Example II as a suppressant in ore flotation. About 750 grams of a Cu/Ni/Fe-containing ore (Falconbridge ore) along with 300 milliliters of tap water and 0.5 grams (1.3 lb/ton) of lime was added to a ball mill and ground for 2 minutes and 52 seconds. The ground mixture was transferred to a 2.5 Liter capacity Denver D-12 flotation cell along with enough water to make about a 30 weight percent aqueous slurry. Also added was 6 drops (0.068 lb/ton) of a frother (Dowfroth 250) and 6 milliliters (0.16 lb/ton) of a 1 weight percent aqueous solution of sodium isopropyl xanthate and the slurry conditioned for 1 minute. After conditioning, the slurry was floated for 7 minutes and the concentrate filtered, dried and analyzed. The procedure was repeated and an average weight percent recovery estimated. In this manner there was obtained average weight percent recoveries of 89.2 percent Cu, 78.6 percent Ni, and 57.1 weight percent Fe.

The procedure was repeated except that in addition to the xanthate collector there was added 1.7 milliliters (5 lbs/ton) of a 40 weight percent aqueous solution of the trithiocarbonate salt prepared in Example II, namely, sodium N,N-diethylaminoethyl-3-(thiocarbonyldithio)propionate. The mixture was conditioned for 2 minutes and floated for 7 minutes. The concentrate was again collected, filtered, dried and analyzed to determine whether the trithiocarbonate salt acted as a suppressant, collector or had no affect. These results are listed in Table I where it can be seen that the inventive trithiocarbonate salt (run 2) greatly suppressed the flotation of Cu, Ni and Fe when compared to the control where only the xanthate reagent (run 1) was used.

TABLE I

Reagent Suppressant Action (Falconbridge Ore)

| Run | Reagent(s) | lb/ton | Av. Wt. % Recovery Cu | Ni | Fe |
|---|---|---|---|---|---|
| | Control: | | | | |
| 1 | Sodium Isopropyl Xanthate | 0.16 | 89.2 | 78.6 | 57.1 |
| | Invention: | | | | |
| 2 | Sodium Isopropyl Xanthate plus | 0.16 | 3.45 | 2.08 | 1.93 |
| | Sodium N,N—Diethylamino-ethyl-3-(thiocarbonyl-dithio)propionate | 5.0 | | | |

EXAMPLE IV

This example describes the procedure used to evaluate the reaction product mixture from Example II as a suppressant in a Mo ore flotation wherein Cu and Fe sulfide minerals are suppressed while Mo continues to be floated. About 1000 grams of a Mo/Cu/Fe-containing ore (Moly. Corp. Questa Mine) along with 660 milliliters of water, 0.1 milliliters (0.2 lb/Ton) diesel oil (Mo collector) and 14 drops (0.1 lb/Ton) frother (6:3 weight ratio of methylisobutylcarbinol:pine oil) was ground in a table ball mill for 6 minutes 42 seconds and transferred to a 2.5 Liter capacity Wemco flotation cell, conditioned 30 seconds at 1500 rpm and floated for 8 minutes. The concentrate at this point is referred to as the rougher float. The rougher float was transferred to a 2.5 Liter capacity Denver flotation cell along with enough water to bring the level of slurry to within 1 or 2 inches of the cell lip. To the cell was added 0.93 milliliters (5 lb/Ton) of the inventive suppressant along with enough lime to maintain a pH of 8.5. The slurry was conditioned for 2 minutes at 1100 rpm whereupon 1 drop (about 0.007 lb/Ton) diesel oil Mo collector and 2 drops (about 0.014 lb/Ton) frother was further added, the slurry conditioned for 30 seconds and floated for 4 minutes. This second float, referred to as the cleaner concentrate, was filtered, dried and analyzed. The procedure was repeated and an average weight percent recovery estimated based on the amount of Mo, Cu, and Fe present in the rougher concentrate. In this manner there was obtained average weight percent recoveries of 67.7 percent Mo, 9.8 percent Cu, and 4.2 percent Fe.

The procedure was then repeated several times using two known suppressants and a control where no suppressant was added. The results are listed in Table II where it can be seen that the inventive trithiocarbonate-ester-amine (runs 7 and 8) greatly suppress the flotation of Cu and Fe while not greatly interfering with the flotation of Mo when compared with runs (1, 2) where no suppressant was employed. The inventive suppressant appears to perform better as a Cu and Fe suppressant than does a known suppressant, NaSH (runs 3 and 4). Compared with another known suppressant, disodium carboxymethyl trithiocarbonate (runs 5, 6), the inventive suppressant gives a higher Mo recovery (indicating less interference) but also a slightly higher recovery of Cu and Fe.

TABLE II

Suppressant Action in a Mo Ore Flotation Process (Questa Mine Ore)

| Run | Suppressant, 5 lb/T solids | % Recovery Mo | Cu | Fe |
|---|---|---|---|---|
| | Control: | | | |
| 1 | No suppressant added | 78.5 | 70.3 | 12.7 |
| 2 | No suppressant added | 75.8 | 62.0 | 6.4 |
| | Av. = | 77.2 | 66.2 | 9.6 |
| 3 | NaSH (40% Aq.) | 77.1 | 70.3 | 15.1 |
| 4 | NaSH (40% Aq.) | 76.5 | 68.4 | 10.0 |
| | Av. = | 76.8 | 69.4 | 12.6 |
| 5 | Disodium Carboxymethyl Trithiocarbonate[a] | 48.5 | 4.7 | 3.3 |
| 6 | Disodium Carboxymethyl Trithiocarbonate[a] | 51.3 | 6.2 | 2.5 |
| | Av. = | 49.9 | 5.5 | 2.9 |
| | Invention: | | | |
| 7 | Trithiocarbonate-Ester-Amine[b] | 70.4 | 11.1 | 4.2 |
| 8 | Trithiocarbonate-Ester-Amine[b] | 65.0 | 8.4 | 4.1 |
| | Av. = | 67.8 | 9.8 | 4.2 |

[a] 40% Aq. solution.
[b] 40% Aq. solution of sodium N,N—diethyl-2-aminoethyl 3-(thiocarbonyldithio)propionate.

In summary, the data herein disclosed reveal that the novel ammonium dialkylaminoalkyl (thiocarbonyldithio) alkanoates and alkali metal dialkylaminoalkyl (thiocarbonyldithio) alkanoates are useful as ore flotation agents. These compounds are particularly suited for suppressing copper and iron in the presence of molybdenum in ore flotation processes. It will further be seen that the novel dialkylaminoalkyl mercaptoalkanoate disclosed herein is extremely useful as an intermediate composition in the production of the novel ammonium dialkylaminoalkyl (thiocarbonydithio) alkanoates and alkali metal dialkylaminoalkyl (thiocarbonyldithio) alkanoates of the present invention.

Reasonable variations and modifications which will become apparent to those skilled in the art can be made in this invention without departing from the spirit and scope thereof.

We claim:

1. A composition represented by the formula $$R^1R^2NR^3O\overset{O}{\overset{\|}{C}}R^4S-\overset{S}{\overset{\|}{C}}-S-M,$$

wherein M is selected from the group consisting of ammonium and alkali metals, wherein $R^1$ is selected from the group consisting of alkyl radicals each having no more than 6 carbon atoms, $R^2$ is selected from the group consisting of alkyl radicals each having no more than 6 carbon atoms, $R^3$ is selected from the group consisting of alkylene radicals each having no more than 6 carbon atoms, $R^4$ is selected from the group consisting of alkylene radicals each having no more than 6 carbon atoms, and $R^1$ and $R^2$ can be the same or different.

2. A composition in accordance with claim 1 wherein $R^1$ is selected from the group consisting of linear alkyl radicals each having from 1 to 6 carbon atoms and branched alkyl radicals each having from 3 to 6 carbon atoms.

3. A composition in accordance with claim 2 wherein $R^2$ is selected from the group consisting of linear alkyl radicals each having from 1 to 6 carbon atoms and branched alkyl radicals each having from 3 to 6 carbon atoms.

4. A composition in accordance with claim 1 wherein $R^3$ is selected from the group consisting of linear alkylene radicals each having from 1 to 6 carbon atoms and branched alkylene radicals each having from 3 to 6 carbon atoms.

5. A composition in accordance with claim 1 wherein $R^4$ is selected from the group consisting of alkylene radicals having from 2 to 6 carbon atoms.

6. A composition in accordance with claim 5 wherein M is sodium.

7. A composition in accordance with claim 4 wherein M is sodium.

8. A composition in accordance with claim 4 wherein $R^4$ is selected from the group consisting of alkylene radicals each having from 2 to 6 carbon atoms, wherein M is sodium, wherein $R^1$ is an ethyl radical, wherein $R^2$ is an ethyl radical, and wherein $R^3$ is an ethylene radical.

9. A composition in accordance with claim 8 wherein $R^4$ is an ethylene radical.

10. Sodium N,N-diethylaminoethyl-3-(thiocarbonyldithio)propionate.

11. A process for producing a novel composition of matter comprising:

reacting $H_2S$ with a composition having the formula $$R^1R^2NR^3O\overset{\overset{O}{\|}}{C}X, \qquad (I)$$

wherein $R^1$ is selected from the group consisting of alkyl radicals each having no more than 6 carbon atoms, $R^2$ is selected from the group consisting of alkylene radicals each having no more than 6 carbon atoms, and X is selected from the group consisting of alkenyl radicals each having no more than 6 carbon atoms, to form a composition having the formula $$R^1R^2NR^3O\overset{\overset{O}{\|}}{C}R^4SH, \qquad (II)$$

wherein $R^4$ is selected from the group consisting of alkylene radicals each having no more than 6 carbon atoms.

12. A process in accordance with claim 11 characterized further to include recovering the composition of formula (II) as the product of the process.

13. A process in accordance with claim 11 characterized further to include distilling the reaction product of the reacting step defined therein to recover the composition of formula (II).

14. A process in accordance with claim 11 characterized further to include reacting the composition of formula (II) with $CS_2$ and a hydroxide having the formula $$MOH \qquad (III),$$

wherein M is selected from the group consisting of ammonium and alkali metals to form a composition having the formula $$R^1R^2NR^3O\overset{\overset{O}{\|}}{C}R^4S-\overset{\overset{S}{\|}}{C}-S-M, \qquad (IV)$$

and recovering the composition of formula (IV) as the product of the process.

15. A process in accordance with claim 14 wherein $R^1$ is an ethyl radical.

16. A process in accordance with claim 15 wherein $R^2$ is an ethyl radical.

17. A process in accordance with claim 16 wherein M is sodium.

18. A process in accordance with claim 11 wherein $R^1$ is an ethyl radical.

19. A process in accordance with claim 18 wherein $R^2$ is an ethyl radical.

20. A process in accordance with claim 19 wherein X is a vinyl radical.

21. A process in accordance with claim 11 wherein X is a vinyl radical.

22. A process for recovering minerals comprising:

(a) mixing crushed ore containing minerals, water and a composition having the formula $$R^1R^2NR^3O\overset{\overset{O}{\|}}{C}R^4S-\overset{\overset{S}{\|}}{C}-S-M,$$

wherein $R^1$ is selected from the group consisting of alkyl radicals each having no more than 6 carbon atoms, $R^2$ is selected from the group consisting of alkyl radicals each having no more than 6 carbon atoms, $R^3$ is selected from the group consisting of alkylene radicals each having no more than 6 carbon atoms, $R^4$ is selected from the group consisting of alkylene radicals each having no more than 6 carbon atoms, and M is selected from the group consisting of ammonium and alkali metals, to establish a pulp;

(b) aerating said thus established pulp to produce a froth containing said minerals; and (c) recovering said minerals from said thus produced froth.

23. A process in accordance with claim 22 wherein $R^1$ and $R^2$ are each selected from the group consisting of linear or branched alkyl radicals, and wherein $R^1$ and $R^2$ can be the same or different.

24. A process in accordance with claim 22 wherein M is sodium, $R^1$ is an ethyl radical and $R^2$ is an ethyl radical.

25. A process in accordance with claim 24 wherein $R^3$ is an ethylene radical and $R^4$ is an ethylene radical.

26. A process in accordance with claim 22 wherein $R^4$ is an ethylene radical.

27. A process for recovering minerals comprising:

(a) mixing crushed ore containing said minerals, water and a composition produced in accordance with the process of claim 14 to establish a pulp;

(b) aerating said thus established pulp to produce a froth containing at least a portion of said minerals; and (c) recovering said minerals from said thus produced froth.

28. The composition produced by the process of claim 11.

29. The composition produced by the process of claim 14.

30. A process for recovering minerals comprising:

(a) mixing crushed ore containing minerals, water and a composition produced by the process of claim 14 to establish a pulp;

(b) aerating said thus established pulp to produce a froth containing at least a portion of said minerals; and (c) recovering said minerals from said thus produced froth.

31. A process in accordance with claim 30 wherein said ore comprises Mo, Cu and Fe, and said composition suppresses Cu and Fe from said froth to enhance the selective recovery of Mo from said froth.

32. A process in accordance with claim 30 wherein said ore comprises Cu, Ni and Fe, and said composition suppresses Cu, Ni and Fe.

33. A process for recovering minerals comprising:

(a) mixing a rougher concentrate containing said minerals, water and a composition produced in accordance with the process of claim 14 to establish a pulp;

(b) aerating the thus established pulp to produce a froth containing at least a portion of said minerals; and (c) recovering said minerals from said thus produced froth.

34. A process in accordance with claim 33 wherein said ore contains Mo, Cu and Fe, and said composition suppresses Cu and Fe from said froth to enhance the selective recovery of Mo from said froth.

* * * * *

UNITED STATES PATENT AND TRADEMARK OFFICE
CERTIFICATE OF CORRECTION

PATENT NO. : 4,515,687

DATED : May 7, 1985

INVENTOR(S) : Clarence R. Bresson et al.

It is certified that error appears in the above-identified patent and that said Letters Patent is hereby corrected as shown below:

Claim 11, column 9, line 38, after "R2" and before "is", insert --- is selected from the group consisting of alkyl radicals each having no more than 6 carbon atoms, R3 ---.

Signed and Sealed this

*Third* Day of *December 1985*

[SEAL]

*Attest:*

DONALD J. QUIGG

*Attesting Officer* *Commissioner of Patents and Trademarks*

UNITED STATES PATENT AND TRADEMARK OFFICE

CERTIFICATE OF CORRECTION

PATENT NO. : 4,515,687

DATED : May 7, 1985

INVENTOR(S) : Clarence R. Bresson et al

It is certified that error appears in the above-identified patent and that said Letters Patent is hereby corrected as shown below:

Add to the first page of patent:

Assignee: Phillips Petroleum Company
Bartlesville, Oklahoma

Signed and Sealed this

Twenty-first Day of June, 1988

*Attest:*

DONALD J. QUIGG

*Attesting Officer*

*Commissioner of Patents and Trademarks*